Figure 1:
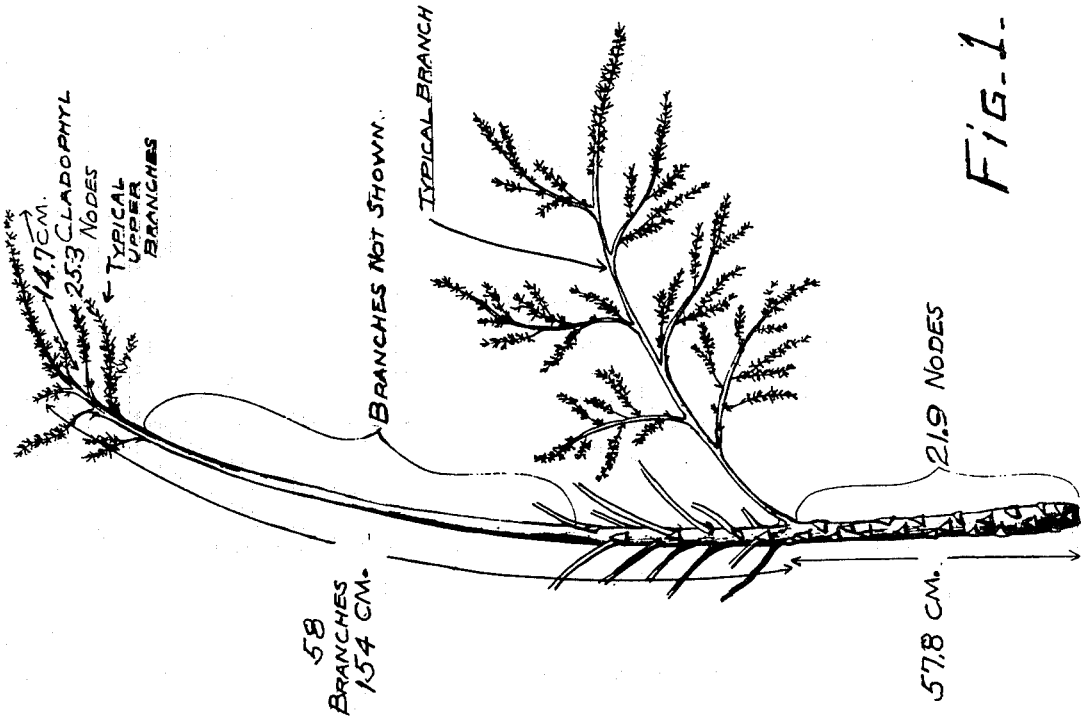

United States Patent [19]

Ellison et al.

[11] Patent Number: Plant 5,550

[45] Date of Patent: Sep. 3, 1985

[54] ASPARAGUS PLANT-GREENWICH-53×22-8

[75] Inventors: J. Howard Ellison, Milltown; John J. Kinelski, Princeton, both of N.J.

[73] Assignee: Rutgers University, New Brunswick, N.J.

[21] Appl. No.: 539,157

[22] Filed: Oct. 5, 1983

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

A hybrid asparagus plant having dominant male characteristics providing volume production characterized by high yield ability as a commercial variety, at the same time being resistant to rust (*Puccinia asparagi*), having a good field tolerance to root rot (*Fusarium oxysporum*) as well as crown rot (*F. moniliforme*) with good adaptability for growth in different areas and under widely varying conditions.

2 Drawing Figures

This invention relates to a new and distinct variety of Asparagus Plant which we have denominated for the purpose of identification and use in the trade by the name "Greenwich", and which is in turn the result or at least one of the products of an intensive program of development including selection, growth and inspection as well as monitoring the ultimate production of a number of varieties of which this particular hybrid is an outstanding example.

As is well known the primary objective in any asparagus program such as we have undertaken and as others undertake likewise, is to produce a variety which will be a heavy producer, having good size spears which will be commercially valuable, and of uniform characteristics both as to size, that is the size relating to the diameter as well as length or height as the case may be.

Additionally of course in order to maintain production and to produce and to result in the aforesaid described desirable spears, the plants must be resistant to the various diseases which are known and which have in many cases adversely affected asparagus growth including the resistance to rust (*Puccinia asparagi*), field tolerance to root rot (*Fusarium oxysporum*) and likewise of course crown rot (*F. moniliforme*).

Where the all male characteristics can be found to be dominant, the most desirable production, quantities and characteristics have been found likewise to be present and thus since the male plants live longer and yield more than female plants, obviously result in more desirable commercial varieties of which this is representative and outstanding, and denominated "Geeenwich" as before indicated.

It may be noted that the parent plants, in this instance the seed parent which is denominated as Plant No. 53, is a selection from a thirty-five year old field of Mary Washington asparagus, the staple and well known variety currently available in commerce and having been for many years a very reliable producer where grown properly and under conditions minimizing some of the undesirable problems which often result from asparagus growth such as those heretofore mentioned.

This selection was made in a field near Greenwich, N.J., we have caused the variety to be asexually reproduced by crown division and tissue culture and have found that it does in fact come true in successive generations.

The pollen parent is known to us as "Super Male" Plant No. 22-8, which is the source of the male characteristics hereof and thus very important being a plant of the first selfed generation seedling from a male plant we know as No. 22 which in turn was also a male parent of the variety "Jersey Centennial" the subject of U.S. Plant Pat. No. 4,998.

Since the program of development of asparagus plants which is carried on by us, is subject to the accumulation of considerable data, we have in fact accumulated such data as is set forth hereinafter.

It may be noted that the data are related to the illustration in the drawing hereof, the drawing showing in FIG. 1, a typical asparagus plant of this variety to which are appended various indicia for reference.

Figure 2:
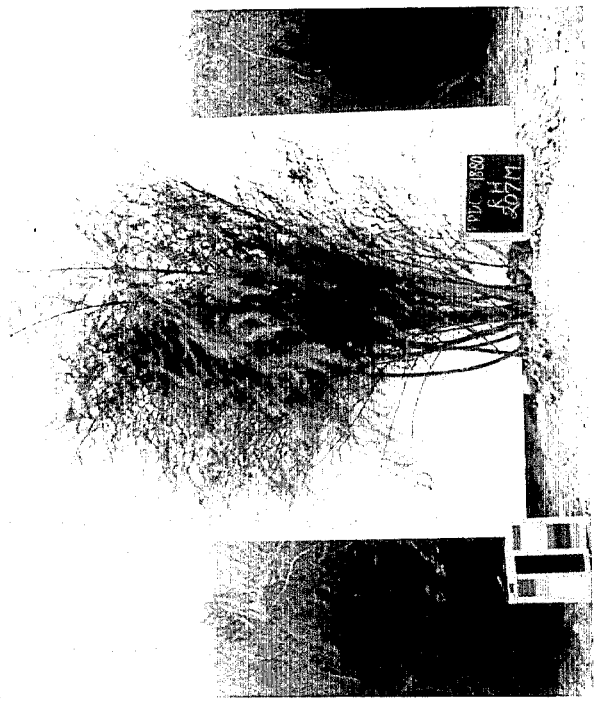

FIG. 2 in the drawing, discloses a typical plant with the color as nearly representative thereof as it is possible to produce in a disclosure of this kind where the color is affected by the density of the plant and thus not in all cases susceptible of specific notation for observation other than by inspection and observation at first hand.

Since the data of production are also important, we have assembled for consideration a table which indicates comparisons in many respects from various areas particularly New Jersey but also in other places, which indicate the wide adaptability of the variety which we have herein disclosed, and indicates particularly and importantly some market information which would be important for any grower and in commercial operation.

Referring therefore to the data first referred to, the same likewise include reference to color which color is selected from the Munsell Limit Color Cascade produced by MacBeth Color and Photometry Div., with notations appropriately referenced thereto.

ASPARAGUS PLANT NO. 53×22-8 MALE HYBRID "GREENWICH"

| Stalk Data | |
|---|---|
| Number of nodes below first branch | 21.9 |
| Number of cm from crown to first branch | 57.8 |
| Number of branches | 58 |
| Number cm between first and last branch | 154 |
| Internode length in cm between branches | 2.66 |
| Number of cladophyll nodes beyond last branch | 25.3 |
| Number of cm beyond last branch | 14.7 |
| Internode length in cm beyond last branch | 0.58 |
| Largest stalk diameter in mm | 20.0 |

-continued

| Flower Data | |
|---|---|
| Petal tip (yellow) | 24–6 |
| Petal base (brown) | 32–13.5 |
| Flower length in mm | 6.12 |
| Flower width at midpoint in mm | 2.65 |

It will be noted from this assembly of information that there are certain very definite aspects, and it is noted that the flower petal base color brown, is particularly outstanding in this variety and suggests the male dominance produced.

Turning to the yield data which are assembled in the next summary, it will be seen that the marketable spears are substantially greater in all cases than comparable and related known varieties, most of which and in fact all of which are not patented as far as is known, the common names of those varieties being used in relation thereto.

TABLE 1

Bridgeton, N.J. Early yield (two weeks) Fusarium infested soil.

| | Jumbo[1] | | | Total Marketable[2] | | |
|---|---|---|---|---|---|---|
| | 1981 | 1982 | Mean | 1981 | 1982 | Mean |
| 53 X 22-8 | 593[4] | 1053 | 823 | 1219 | 1752 | 1486 |
| Mary Washington | 137 | 199 | 168 | 494 | 809 | 652 |

In view of the foregoing, it will be seen that we have described for information and identification the various outstanding aspects of this new variety which will be known as "Greenwich" and which should be and undoubtedly will be a very well accepted commercial plant for continuing production.

We claim:

1. A new and distinct variety of Asparagus Plant as herein shown and described, distinguished particularly as to novelty by the unique combination of homo-genetic characteristics resulting in longer life, with substantially greater production under widely varying conditions of cultivation, having good resistance to rust (*Puccinia asparagi*), good field tolerance to root rot (*Fusarium oxysporum*) and also to crown rot (*F. moniliforme*).

* * * * *